United States Patent [19]

Bruns et al.

[11] Patent Number: 4,528,126
[45] Date of Patent: Jul. 9, 1985

[54] 2,4-DIOXA-7,10-METHANO-SPIRO [5,5] UNDECANES AND THEIR USE IN PERFUMERY COMPOSITIONS

[75] Inventors: Klaüs Bruns; Thuy N. Dang, both of Krefeld-Traar, Fed. Rep. of Germany

[73] Assignee: Henkel Kommanditgesellschaft auf Aktien, Düsseldorf-Holthausen, Fed. Rep. of Germany

[21] Appl. No.: 538,938

[22] Filed: Oct. 4, 1983

Related U.S. Application Data

[63] Continuation of Ser. No. 271,605, Jun. 8, 1981, abandoned.

[30] Foreign Application Priority Data

Jul. 3, 1980 [DE] Fed. Rep. of Germany ....... 3025187

[51] Int. Cl.³ ..................... A61K 7/46; C07D 319/06
[52] U.S. Cl. ................. 252/522 R; 549/336
[58] Field of Search ..................... 549/336; 252/522 R

[56] References Cited

U.S. PATENT DOCUMENTS 4,113,664  9/1978  Conrad et al. ................. 252/522 R
4,294,727 10/1981  Conrad et al. ................. 252/522 R
4,331,569  5/1982  Inoue et al. .................... 252/522 R
4,331,570  5/1982  Klemarczyk et al. .......... 252/522 R

OTHER PUBLICATIONS

Kasper et al., "Chem. Abst.", vol. 92 (1980) 75936t.

Primary Examiner—Anton H. Sutto
Attorney, Agent, or Firm—Hammond & Littell, Weissenberger & Dippert

[57] ABSTRACT 2,4-dioxa-7,10-methano-spiro [5,5] undecanes having the formula

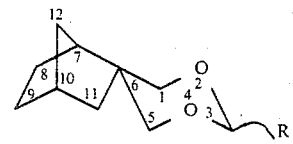

wherein R is a member selected from the group consisting of hydrogen, alkyl having from 1 to 4 carbon atoms, vinyl and propenyl and their isomeric mixtures; its synthesis, its use as a perfumery agent and as an olefactant component in perfumery compositions and as an odorant for technical products.

4 Claims, No Drawings

2,4-DIOXA-7,10-METHANO-SPIRO [5,5] UNDECANES AND THEIR USE IN PERFUMERY COMPOSITIONS

BACKGROUND OF THE INVENTION

This application is a continuation of co-pending U.S. patent application Ser. No. 271,605, filed June 8, 1981, now abandoned.

This invention relates to 2,4-dioxa-7,10-methanospiro[5,5]undecanes having the formula

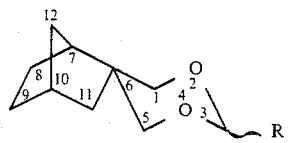

wherein R is a member selected from the group consisting of hydrogen, alkyl having from 1 to 4 carbon atoms, vinyl and propenyl and their isomeric mixtures. These compounds are excellent new odorants for the production of valuable composition for perfuming cosmetic preparations and cleansers.

OBJECTS OF THE INVENTION

An object of the present invention is the obtaining of 2,4-dioxa-7,10-methano-spiro[5,5]undecanes having the formula

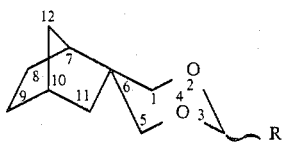

wherein R is a member selected from the group consisting of hydrogen, alkyl having from 1 to 4 carbon atoms, vinyl and propenyl and their isomeric mixtures.

Another object of the present invention is the development of a process for the production of said 2,4-dioxa-7,10-methano-spiro[5,5]undecanes.

A further object of the present invention is the development of a perfumery composition containing essentially of from 1% to 50% by weight of said 2,4-dioxa-7,10-methano-spiro[5,5]undecanes and the remainder customary constituents of perfumery compositions.

A yet further object of the present invention is the development of a method of imparting a pleasant odor to a product comprising adding a sufficient amount of the above perfumery composition to provide the desired degree of odor.

These and other objects of the invention will become more apparent as the description thereof proceeds.

DESCRIPTION OF THE INVENTION

The above objects have been achieved by the novel 2,4-dioxa-7,10-methano-spiro[5,5]undecanes having the formula

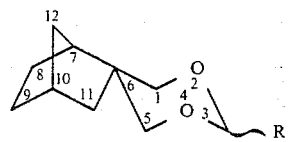

wherein R is a member selected from the group consisting of hydrogen, alkyl having from 1 to 4 carbon atoms, vinyl and propenyl and their isomeric mixtures.

The manufacture of the new compounds of the invention is effected by known methods of organic synthesis is several stages, where in the first step cyclopentadiene is reacted with acrolein to give norborn-5-ene-2-carbaldehyde, the latter is subjected in the second step to methylolization according to Canizzaro in an alkaline medium to give 2,2-di-hydroxymethylnorborn-5-ene, the double bond is catalytically hydrogenated in a third step, and the spirocetal of the invention is obtained in a fourth step by subsequent acetalization with appropriate aldehydes.

The reaction takes place according to the following reaction scheme:

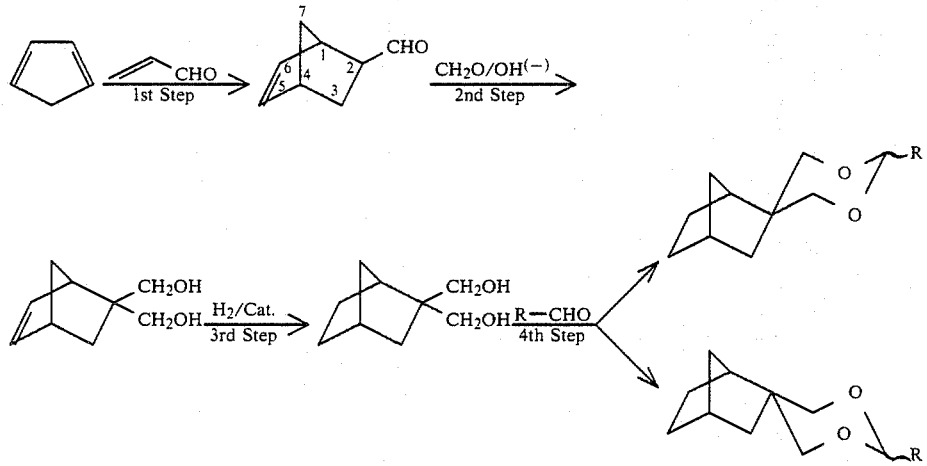

where R has the above assigned values.

The new 2,4-dioxa-7,10-methano-spiro[5,5]undecanes are obtained as a mixture of stereo-isomeric forms and are used as such as perfumes and employed as a component in perfume compositions.

As new perfumes according to the invention are mentioned, for example, 2,4-dioxa-7,10-methano-spiro[5,5]undecane, 2,4-dioxa-3-methyl-7,10-methano-spiro[5,5]undecane, 2,4-dioxa-3-ethyl-7,10-methano-spiro[5,5]undecane, 2,4-dioxa-3-isopropyl-7,10-methanospiro[5,5]-undecane, 2,4-dioxa-3-vinyl-7,10-methano-spiro[5,5]undecane, 2,4-dioxa-3-propenyl-7,10-methano-spiro[5,5]undecane, etc.

The new perfumes of the invention are characterized by their intensive, interesting different scents of high olfactory quality and richness. Another advantage of the new perfumes is their very good ability to combine to give novel odor nuances.

The new perfumes of the invention can be mixed with other fragrances in a variety of ratios to form new perfumery compositions. Generally, however, the proportion of the new odorants in the perfume compositions will range from 1% to 50% by weight, related to the total composition.

Such compositions can be used directly as perfumes or for perfuming cosmetic preparations such as soaps, etc. They also may be used to improve the smell of technical products such as washing and cleaning agents, disinfectants, and agents for the treating of textiles. For the scenting of the various products, the compositions generally are added to the former in concentrations of 0.05% to 5% by weight, related to the total product.

The following examples illustrate the subject matter of the invention in more detail without limiting it, however, to these examples.

EXAMPLES

First the manufacture of the new odorants are described.

EXAMPLE 1

2,4-Dioxa-3-methyl-7,10-methano-spiro[5,5]undecane

1st Step: Preparation of norborn-5-en-2-carbaldehyde 33.05 gm of freshly distilled cyclopentadiene, obtained by distillation of bicyclopentadiene over a 50 cm Vigreux column at normal pressure, were charged and then 28.03 gms of acrolein were added in drops over a period of 30 minutes under stirring. As soon as the temperature exceeded 55° C., the reaction vessel was cooled in ice water. After the addition was completed, the stirring was continued for another 3 hours at 60° C. The mixture was subsequently distilled under a water jet vacuum. The intermediate product, norborn-5-en-2-carbaldehyde was obtained with a yield of 73.8% of the theory, and had the following characteristics.

$Bp_{17}$ 61° C.; GC: 89.3/10.6%

IR (film): 2710, 1720/cm (CHO); 3060, 720/cm (cis—HC=CH).

$^1H$—NMR(CDCl$_3$): 9.47 ppm (d, 1H) (C$\underline{H}$O); 6.18 ppm (double d, 2H) (H$\underline{C}$=C$\underline{H}$)

2nd Step: Preparation of 2,2-dihydroxymethyl-norborn-5-ene 25 gm of norborn-5-en-2-carbaldehyde were added in drops to a mixture of 42 ml of 37% formalin and 12.3 gm of sodium hydroxide, dissolved in 36.9 ml of water, under stirring under a nitrogen atmosphere and water cooling over a period of 25 minutes. The temperature of the reaction mixture rose to 30° C. Subsequently the stirring was continued for another hour at 55° C., and then the reaction mixture was extracted with 50 ml of methylisobutyl ketone. The organic phase was washed with 50 ml of water, and the aqueous phase with 50 ml of methylisobutylketone. The combined organic phases were washed neutral, dried over sodium sulfate, and the solvent was distilled off. The residue was recrystallized from petroleum-ether (60-95)/toluene (1:1). The intermediate product, 2,2-di-hydroxymethyl-norborn-5-ene, was obtained in the form of colorless crystals with a yield of 77.6% of the theory, and had the following characteristics:

Mp 113.5°–115° C.

IR (KBr): 3300/cm (OH); 1037,1018/cm (prim. OH); 3060, 715/cm (cis—HC=CH—).

$^1H$—NMR(d$^6$—DMSO): 6.16 ppm, (m, 2H) (H$\underline{C}$=C$\underline{H}$): 4.40 ppm (2t, 2H) (O$\underline{H}$); 3.40 ppm (m, 4H) (C$\underline{H}_2$OH); 0.59 ppm (2d, 1H) (C$_7$—$\underline{H}$).

3rd Step: Preparation of 2,2-di-hydroxymethyl-norbornane 155 gm of 2,2-dihydroxyethyl-norborn-5-ene (1.0 mol) were dissolved in 400 ml of methanol in an autoclave, mixed with 14.2 gm of Raney nickel, and hydrogenated at 45° C. and 70 bar hydrogen pressure for 5 hours until saturation of the double bond. After removing the catalyst and the solvent, 2,2-di-hydroxymethyl-norbornane remained in a quantitative yield in the form of colorless crystals with the following characteristics:

Mp 97°–98° C.

IR(KBr) 3330/cm (OH), 1020/cm (prim. OH)

$^1H$—NMR (CDCl$_3$): 3.65 ppm (2m, 5H) (C$\underline{H}_2$OH): 0.72 ppm (2d, 1H) C$_7$—$\underline{H}$).

4th Step: Preparation of 2,4-dioxa-3-methyl-7,10-methano-spiro[5,5]undecane

A mixture of 90.8 gm of 2,2-di-hydroxymethyl-norbornane, 86.1 gm of triethylorthoformate and 25.6 gm of acetaldehyde (molar ratio 1:1:1) was mixed with 0.1 gm of p-toluene-sulfonic acid with slight heating. After stirring over night at room temperature, ethyl formate and ethanol were distilled off. The residue was taken up in ether, washed with 2N-sodium carbonate solution and water, and dried over sodium sulfate. After distilling off the solvent, the residue was distilled under the water jet vacuum. The 2,4-dioxa-3-methyl-7,10-methano-spiro[5,5]undecane was obtained with a 90% yield as a colorless liquid had the following characteristics:

$Bp_{17}$ 110° C.; GC 78.4/21.1%; $n_D^{20}$ 1.4822.

IR (film): 1150, 1100, 1025/cm (—O—C—O); 1405/cm (CH$_3$)

$^1H$—NMR (CDCl$_3$): 4.60 ppm (q, 1H) (C$_3$—$\underline{H}$), 3.68 ppm (2m, 4H) (C$\underline{H}_2$—O—CH(CH$_3$)—O—C$\underline{H}_2$); 0.63 ppm (2d, 1H) (C$_{12}$—$\underline{H}$).

The product, which is a mixture of two stereoisomers, has a rhubarb-galbanum odor.

EXAMPLE 2

2,4-Dioxa-7,10-methano-spiro[5,5]undecane

The preparation was similar as in Example 1, but instead of acetaldehyde the acetalization was effected in the 4th step directly with the corresponding amounts of paraformaldehyde in ethylene chloride. The end product obtained as a coloress liquid had the following characteristics:

$Bp_{17}$ 104° C.; $n_D^{20}$ 1.4932, MW: 168 (MS homogenous); odor minty, methone-scent.

EXAMPLE 3

2,4-Dioxa-3-ethyl-7,10-methano-spiro[5,5]undecane

The preparation was similar as in Example 1, but instead of acetaldehyde a corresponding amount of propionaldehyde was used in the 4th step. The end product obtained as a colorless liquid had the following characteristics:

Bp$_{17}$ 120° C., n$_D^{20}$ 1.4813, MW: 196 (GC/MS: 2 stereoisomers) odor: woody, flowery, sweet, artificial honey, boysenberry scent.

EXAMPLE 4

2,4-Dioxa-3-i-propyl-7,10-methano-spiro[5,5]undecane

The preparation was similar as in Example 1, but instead of acetaldehyde, a corresponding amount of isobutyraldehyde was used in the 4th step. The end product obtained is a colorless liquid with the following characteristics:

Bp$_{17}$ 128° C., n$_D^{20}$ 1.4783, MW: 210 (GC/MS: 2 stereoisomers) odor: earthy, woody, sweet.

EXAMPLE 5

2,4-Dioxa-3-vinyl-7,10-methano-spiro[5,5]undecane

The preparation was similar as in Example 1, but instead of acetaldehyde, the corresponding amount of acrolein was used in the 4th step. The end product obtained in a colorless liquid with the following characteristics:

Bp$_1$ 84° C., n$_D^{20}$ 1.4955, MW: 194 (GC/MS: 2 stereoisomers) odor: flowery, honey, diphenylether scent.

EXAMPLE 6

2,4-Dioxa-3-propenyl-7,10-methano-spiro[5,5]undecane

The preparation was similar as in Example 1, but instead of acetaldehyde a corresponding amount of crotonaldehyde was used in the 4th step. The end product obtained is a colorless liquid with the following characteristics:

Bp$_{0.8}$ 93° C., n$_D^{20}$ 1.4956, MW: 208 (GC/MS: 4 stereoisomers). odor: oily, sweet, sandalwood scent.

The compounds mentioned in the foregoing examples are suitable for the production of the various perfume compositions, which are used for perfuming various products, like cosmetics, detergents, soaps, but also technical products in concentrations of 0.05 to 2% by weight. Here are other examples of perfume compositions containing compounds according to the invention:

EXAMPLE 7

| Hyacinth composition | |
|---|---|
| 2,4-dioxa-3-methyl-7,10-methano-spiro-[5,5] undecane | 150 parts by weight |
| Benzyl acetate | 150 parts by weight |
| Linalool | 150 parts by weight |
| Cinnamyl alcohol | 100 parts by weight |
| Phenylethyl alcohol | 90 parts by weight |
| Hydroxycitronellal | 90 parts by weight |
| Heliotropine | 50 parts by weight |
| Benzyl alcohol | 40 parts by weight |
| Phenylacetaldehyde | 30 parts by weight |
| Ylang-Ylang oil | 25 parts by weight |
| Dimethylbenzylcarbinyl acetate | 20 parts by weight |
| Eugenol | 15 parts by weight |
| Cinnamyl acetate | 15 parts by weight |
| Isoeugenol | 10 parts by weight |
| α-Irone | 10 parts by weight |

| -continued | |
|---|---|
| Hyacinth composition | |
| Phenylacetaldehyde-dimethylacetal | 10 parts by weight |
| Citronellol | 10 parts by weight |
| Trans-2-hexenal (10% i.DEP) | 10 parts by weight |
| Hexenyl benzoate | 5 parts by weight |
| Rose oxide | 5 parts by weight |
| Cyclamen aldehyde | 5 parts by weight |
| Methyloctynylcarbonate (10% i. DEP) | 5 parts by weight |
| N—methyl-methylanthranilate | 5 parts by weight |
| | 1000 parts by weight |

EXAMPLE 8

| Honey-flower-variant | |
|---|---|
| 2,4-Dioxa-3-vinyl-7,10-methano-spiro-[5,5] undecane | 100 parts by weight |
| Phenylethyl alcohol | 350 parts by weight |
| Phenylethyl phenylacetate | 150 parts by weight |
| Cinnamyl alcohol | 100 parts by weight |
| Hydroxycitromellal | 60 parts by weight |
| Heliotropine | 50 parts by weight |
| Propylphenyl acetate | 50 parts by weight |
| Phenylethyl salicylate | 35 parts by weight |
| Linalool | 30 parts by weight |
| Methyl phenylacetate | 30 parts by weight |
| p-methylquinoline | 20 parts by weight |
| Methyleugenol | 5 parts by weight |
| Vanillin | 5 parts by weight |
| Coumarin | 5 parts by weight |
| Ethyl pelargonate | 5 parts by weight |
| Citronellol | 5 parts by weight |
| | 1000 parts by weight |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. 2,4-dioxa-7,10-methano-spiro[5,5]undecanes having the formula

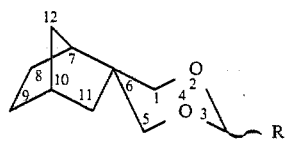

wherein R is a member selected from the group consisting of hydrogen, alkyl having from 1 to 4 carbon atoms, vinyl and propenyl and their isomeric mixtures.

2. A perfumery composition consisting essentially of from 1% to 50% by weight of the 2,4-dioxa-7,10-methano-spiro[5,5]undecane of claim 1 and the remainder customary constituents of perfumery compositions.

3. The method of imparting a pleasant odor to a product comprising the step of adding a sufficient amount of the perfumery composition according to claim 2 to provide the desired degree of odor.

4. The method of claim 3 wherein the effective amount consists of from 0.05% to 5% by weight of the composition of claim 2.

* * * * *